Figure 1:
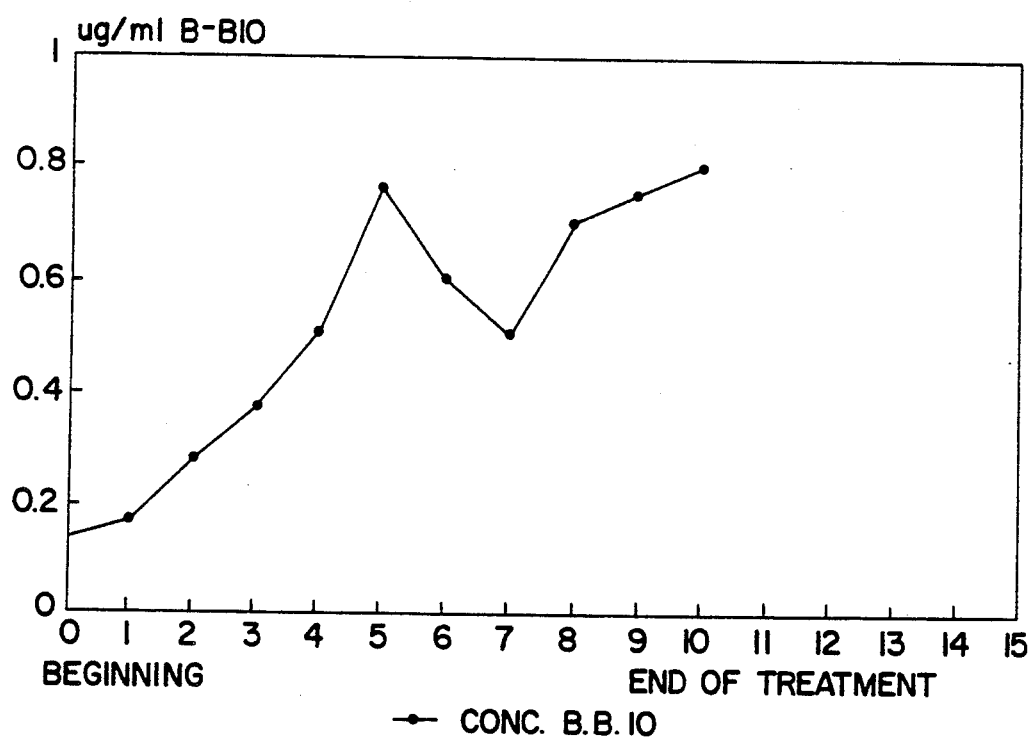

United States Patent [19]

Wijdenes et al.

[11] Patent Number: 5,084,391

[45] Date of Patent: Jan. 28, 1992

[54] MONOCLONAL ANTIBODY TO THE INTERLEUKIN-2-RECEPTOR AND ITS USE

[75] Inventors: John Wijdenes, Geneuille; Patrick Herve, Franois; Claude Clement, Gray; Brigitte Morel-Fourrier; Andre Peters, both of Besancon, all of France

[73] Assignee: Centre Regional de Transfusion Sanguine, Besancon, France

[21] Appl. No.: 343,091

[22] Filed: Apr. 25, 1989

[30] Foreign Application Priority Data

May 6, 1988 [DE] Fed. Rep. of Germany ....... 3815472

[51] Int. Cl.$^5$ .................. C12N 5/20; C07K 15/28
[52] U.S. Cl. .................. 435/240.27; 435/70.21; 435/172.2; 435/7.92; 530/387; 530/388; 424/85.2; 424/85.8
[58] Field of Search .............. 435/7, 7.91, 7.92, 70.21, 435/172.2, 240.27; 530/350, 387–389; 935/100, 104, 107, 110; 424/85.2, 85.8

[56] References Cited

U.S. PATENT DOCUMENTS 4,578,335  3/1986  Urdal et al. .................. 435/68

OTHER PUBLICATIONS

Köhler & Milstein, "Continuous Cultures of Fused Cells Secreting Antibody of Predefined Specificity", Nature, vol. 256 (1975) 495–497.

Anasetti, Martin et al., "A Phase I–II Study Evaluating the Murine Anti–IL-2 . . . ", Transplantation (1990), pp. 49–54.

Herve, Wijdenes et al., "Treatment of Corticosteroid Resistant Acute Graft-Versus-Host . . . ", Blood, vol. 75 (1990), pp. 1017–1023.

Transplantation Proceedings, vol. 23, No. 1 (Feb.) 1991, pp. 1692–1694.

The Lancet, Nov. 5, 1988, pp. 1072–1073.

*Primary Examiner*—Margaret Moskowitz
*Assistant Examiner*—Robert D. Budens
*Attorney, Agent, or Firm*—Sprung Horn Kramer & Woods

[57] ABSTRACT

New monoclonal murine-IgG$_1$ antibody obtainable from a new hybridoma-cell line, binding to an epitope of the human interleukin-2 receptor that differs from Tac, inhibiting the binding of human interleukin-2 to its receptor, and appropriate for the treatment, prophylaxis, and diagnosis of interleukin-2-dependent diseases in humans.

5 Claims, 2 Drawing Sheets

MONOCLONAL ANTIBODY TO THE INTERLEUKIN-2-RECEPTOR AND ITS USE

The invention concerns a new line of hybridoma cells and a monoclonal antibody derived therefrom that recognizes an antigen on activated T cells, the interleukin-2 receptor, and inhibits the proliferation dependent on interleukin-2.

The invention also concerns the use of this monoclonal antibody for therapeutic and diagnostic purposes.

Interleukin-2, originally called T-cell growth factor (TCGF: L. A. Aarden, J. Immunol. 123 [1979], 2928) is one of the essential mediators of cellular response.

The immune response mediated by interleukin-2 results from its interaction with a high-affinity cellular-surface receptor. This interleukin-2 receptor consists of two non covalently linked polypeptides: a light chain ($M_r=55$ kDA, Tac-antigen) and a heavy chain ($M_r=75$ kDa). It has been demonstrated (K. A. Smith, Immunology Today 9 [1988], 36) that both the light and the heavy component exhibit a binding affinity with interleukin-2 ($K_D=10^{-8}$ M for the light and $10^{-9}$ for the heavy component). Both subunits constitute the high-affinity interleukin-2 receptor with a binding constant of $10^{-11}$ M.

Specific substances that suppress the affinity of interleukin-2 to the receptor, by interacting with either the smaller subunit or the longer chain, are necessary to inhibit the interacting of interleukin-2 to its receptor. Monoclonal antibodies that can be prepared by known methods (C. Milstein & G. Köhler, Nature 256 [1975], 495) have been proven appropriate for this purpose. The monoclonal antibodies obtained in this way recognize specific epitopes of the interleukin-2 receptor molecule. Three epitopes on the light chain have so far been identified (T. Diamantstein, Behring Inst. Mitt. 81 [1987], 73).

Uchiyama et al (J. Immunol. 126[1981], 1398) described the first monoclonal antibody to recognize the Tac-antigen (epitope), the short chain of the interleukin-2 receptor.

European Application 0 241 811 describes two monoclonal antibodies also obtained by the aforesaid method. They react specifically with activated T and B cells but are inactive against quiescent lymphocytes. One of these monoclonal antibodies, an anti-Tac analogue, enters into interaction with the Tac-antigen, the shorter chain of the receptor molecule. The other monoclonal antibody also obviously enters into interaction with the smaller subunit of the receptor. It recognizes, however, a determinant that differs from the Tac-epitope. It inhibits not only interleukin-2 dependent proliferation but also the binding of the interleukin-2 to the interleukin-2 receptor. The effectiveness of this monoclonal antibody in clinical trials however, has not yet been demonstrated.

European Application 0 240 344 concerns anti-CD 4 monoclonal antibodies and anti-Tac analogues (CD 25). Its activity with respect to immunosuppression and specifically with respect to prevention of rejection of transplants has been tested in mice and rats.

It is, however, impossible to correlate the results to interleukin-2 dependent reactions in humans because the aforesaid monoclonal antibodies are species specific and effective only against the mouse interleukin-2 receptor, meaning that no clinical trials with these antibodies can be done.

J. P. Soulillou et al (The Lancet, 6/13/87, 1339) has described the activity of a monoclonal antibody against the human interleukin-2 receptor in combating kidney-transplant rejection. The mechanism of interaction of this monoclonal antibody, called 33B3.1, is not known. Furthermore, relatively high doses are necessary and significant side effects (fever, incompatibility, and antibody formation) frequently occur due to the high amount of mouse protein.

The object of this invention is to provide a monoclonal antibody that will be suitable for effective inhibiting, repressing, or suppressing all the interleukin-2 dependent steps in human immunodefense and at the same time attaining a long lasting tolerance of the tissue recognized as foreign. This monoclonal antibody is to be both prophylactically and therapeutically effective at such low doses that very weak or no side effects will occur during or after treatment.

This object is attained in accordance with a known method developed by C. Milstein and G. Köhler in isolating a new line of hybridoma cells that produces a murine monoclonal antibody of the $IgG_1$ class against the human interleukin-2 receptor. From this cell line, which is deposited in the French National Collection of Microorganism Cultures (CNCM) under number I-752, such class-switch variants of the murine immunoglobulins such as $IgG_{2a}$ and $IgG_{2b}$, $IgG_3$, and IgM for example and other immunoglobulin classes can be isolated.

The monoclonal antibody in accordance with the invention, which will be called B.B.10 hereinafter, competes with the binding of interleukin-2 to the interleukin-2 receptor on human T cells and inhibits the interleukin-2-induced proliferation of active T cells. This antibody also inhibits the human mixed-lymphocytes reaction. It has also been demonstrated that the monoclonal antibody binds to an epitope of the human interleukin 2 receptor that is not Tac. The antibody is accordingly appropriate for the treatment of and prophylaxis against such diseases as hyperimmune syndrome, graft-versus-host disease, and host-versus-graft disease, for transplanting bone marrow, kidneys, hearts, lungs, pancreases, skin, livers, etc., for T-cell dependent allergic and autoimmune diseases (myocarditis, diabetes, myasthenia gravis, lupus erythematosus, Crohn's disease, multiple sclerosis, AIDS, encephalomyelitis, arthritis, etc.), and for interleukin-2 receptor expressing tumor diseases such as T-cell leukemia.

The monoclonal antibody can be employed either as such, coupled with magnetic beads, radioactive substances, or pharmaceuticals, or encapsulated in liposomes.

The B.B.10 monoclonal antibody is also appropriate as a diagnostic reagent for detecting the human interleukin-2 receptor on the surface of cells or in body fluids. The monoclonal antibody in accordance with the invention can be employed to identify cells that express interleukin-2 receptors. In such applications, the monoclonal antibody is preferably coupled to fluorescent or other coloring substances or to a radioactive substance, or another labelled antibody specific to murine immunoglobulin is employed.

It is also possible in conjunction with another anti-interleukin-2 receptor antibody to develop an ELISA or radioimmunoassay to measure the free and dissolved interleukin-2 receptor in the body fluids.

The monoclonal antibody in accordance with the invention is also appropriate for producing chimeras with a constant component of human origin (human immunoglobulin) and a variable and especially hypervariable component of murine origin. The chimeras can be employed as such or coupled with magnetic beads, radioactive substances, or other pharmaceuticals or encapsulated in liposomes, either for the treatment of or prophylaxis against interleukin-2 dependent diseases in humans.

Figure 2:
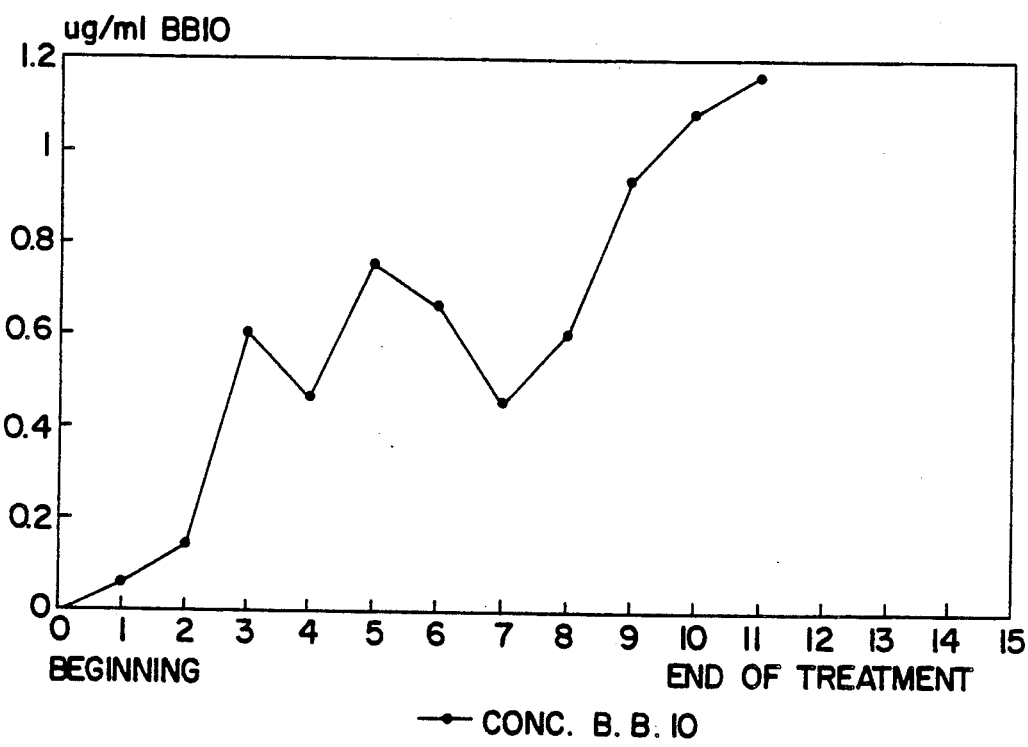
Figure 3:
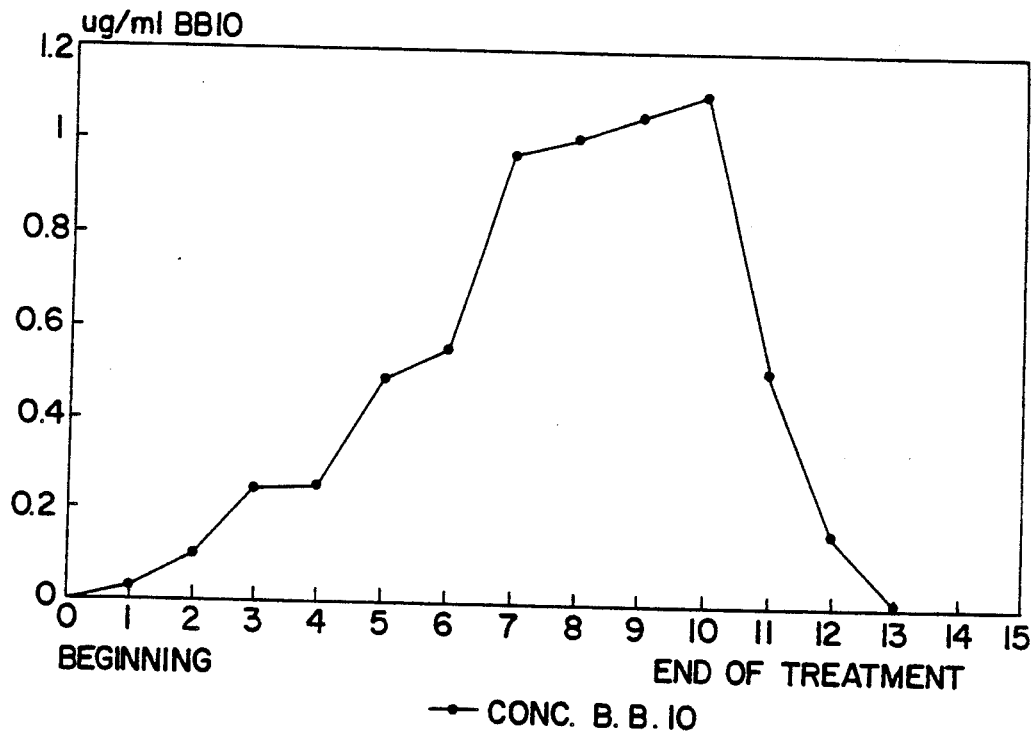
Figure 4:
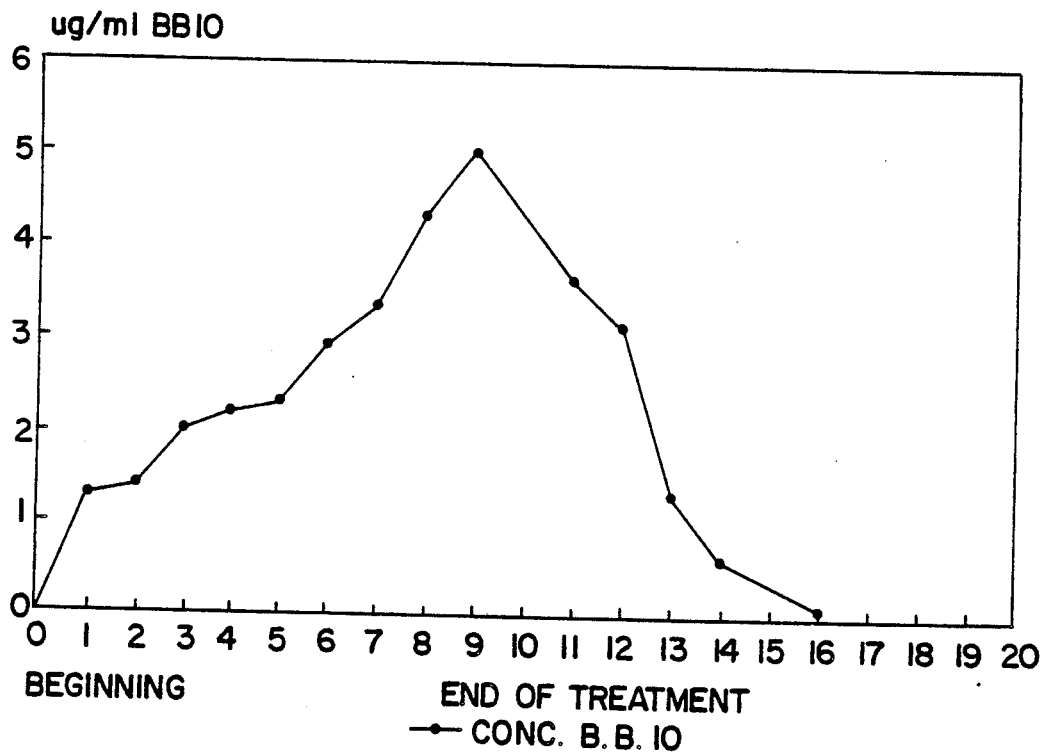

The invention will now be described with reference to the following examples appended drawings, wherein FIGS. 1 to 4 each is a plot showing the B.B.10 serum level of a different patient as a function of days after treatment was begun and terminated.

PREPARING THE MONOCLONAL ANTIBODY

Example 1

Preparing the antigen (IL-2 receptor)

T cells from human peripheral-blood lymphocytes (PBL) were isolated by sheep-erythrocyte rosetting and incubated for 4 days at 37° C. in a culture medium (RPMI 1640, 10% fetal-calf serum [FCS: Lot 126075, mfg. Flow], and 10 µg/ml of phytohemagglutinin [PHA] in an incubator (5% $CO_2$, 95% humidity). The cells cultured in this way were employed in what follows as a source of the human interleukin-2 receptor, called PHA/PBL hereinafter.

Example 2

Immunizing, fusing, cloning, and harvesting monoclonal antibody B.B. 10

Female BALB/c mice were intraperitoneally immunized 3 times at 2-week intervals with $5 \times 10^6$ PHA/PBL. The third immunization was intravenous. The spleen cells were removed 4 days later and fused as will now be described.

The immunized spleen cells were fused with AG 8653 mouse-myeloma cells at a ratio of 5:1 in the presence of polyethylene glycol (Kearney at al., J. Immunol. 123 [1978], 1548). The suspension of fused cells was washed once and cultivated in a selection medium (RPMI 1640, 10% heat-inactivated equine-serum, 4 mM of glutamine, HAT: hypoxanthine 13.6 mg/1, aminopterin 0.17 mg/1, and 10 µg/ml insulin). 10 days after fusion, supernatants that exhibited hybridoma growth were tested for anti-interleukin-2 receptor monoclonal-antibody production by incubating PHA/PBL's ($3 \times 10^5$ in 50 µl of 1% bovine-serum albumin/PBS) with 10 µl of test residue or control monoclonal antibody. The control monoclonal antibodies in this and in the following examples were the anti-Tac-analogous monoclonal antibodies BF 2 and BG 8 (CRTS, Besancon). The bound monoclonal antibody was detected with an FITC-conjugated anti-mouse antibody using a cytofluorometer (Ortho 50H, mfg. Ortho). Of 1187 supernatants tested, 8 exhibited a significant binding to activated T cells and no binding to quiescent T cells. Subsequent to 4 cloning steps using the limiting-dilution method (dissemination density 0.2 cells/culture), the B.B.10 clone was isolated.

B.B.10 is a murine-$IgG_1$ monoclonal antibody with a kappa light chain and exhibits significant binding to activated human T cells.

Example 3

In vivo production and purification of the B.B. 10 monoclonal antibody

The anti-interleukin-2 receptor monoclonal antibody B.B.10 was produced in vivo in large volumes by intraperitoneal injection of BALB/c mice with B.B.10 hybridoma cells. One week before the hybridoma-cell injection, the mice were intraperitoneally primed with 1.0 ml of pristane. 8 to 14 days after the hybridomacell injection it was possible to obtain ascites.

The monoclonal antibody was then precipitated from the ascites with ammonium sulfate (45% saturation), rebuffered in 0.02 mM tris, pH 7.7, and bound to a Q-sepharose column. The monoclonal antibody was washed on this column with 1% Tween 20 in 0.02 mM of tris, pH=7.7, and eluted from the column with 0.35 M of NaCl (pH=7.7).

For therapeutic purposes the monoclonal antibody was rebuffered in a PBS buffer (phosphate-buffered saline).

THE BIOLOGICAL ACTIVITY OF THE MONOCLONAL ANTIBODY

EXAMPLE 4a

Inhibition of the interleukin-2 induced proliferation of activated T cells with the B.B.10 monoclonal antibody PHA-activated T cells ($5 \times 10^4$/culture) were cultivated for 24 hours in RPMI 1640, 10% fetal-calf serum. Initially, the amounts of interleukin-2 (IL-2: Lymphocult-T ®, mfg. Biotest), B.B.10, the control monoclonal antibodies BF 2 and BG8, and $H^3$-thymidine indicated in Tables 1 and 2 were added to the medium. DNA synthesis, an indicator of cell growth or inhibition, was determined in terms of $H^3$-thymidine incorporation by measuring radioactivity with standard liquid scintillation counting.

Tables 1 and 2a summarize the results.

TABLE 1

| IL-2 U/well | MAb µg/well | Measured radioactivity cpm ± SD | | |
|---|---|---|---|---|
| | | B.B.10 | BF 2 | BG 8 |
| 0 | 0 | 570 ± 140 | n.d. | n.d. |
| 1 | 0 | 3554 ± 140 | | |
| | $10^{-2}$ | 2117 ± 142 | 2734 ± 143 | 3789 ± 147 |
| | $10^{-1}$ | 1430 ± 147 | 2401 ± 145 | 1430 ± 159 |
| | 1 | 913 ± 150 | 1595 ± 148 | 1077 ± 158 |
| | 10 | 943 ± 151 | 1099 ± 144 | 1099 ± 163 |
| 10 | 0 | 5250 ± 140 | | |
| | $10^{-2}$ | 4786 ± 139 | 6475 ± 143 | 6413 ± 145 |
| | $10^{-1}$ | 3907 ± 142 | 4879 ± 141 | 6759 ± 148 |
| | 1 | 3220 ± 141 | 5175 ± 146 | 4249 ± 151 |
| | 10 | 3423 ± 143 | 4106 ± 143 | 4312 ± 155 | cpm = disintegration pr minute, mean of two measurments ± standard deviation
n.d. = not determined
U = reltive biological activity fo interleukin-2 in terms of the preliminary international reference (D.C. Dumonde & B.W. Papermaster, Lymphokin Research 3 [1984], 227)

TABLE 2a

| Interleukin-2 U/well | B.B.10 µwell | Radioactivity cpm ± SD |
|---|---|---|
| 0 | 0 | 473 ± 237 |
| 1 | 0 | 2788 ± 139 |
| 1 | $2 \times 10^{-4}$ | 2635 ± 136 |
| 1 | $2 \times 10^{-3}$ | 1698 ± 144 |
| 1 | $2 \times 10^{-2}$ | 461 ± 154 |
| 1 | $2 \times 10^{-1}$ | 268 ± 177 |

TABLE 2a-continued

| Interleukin-2 U/well | B.B.10 μwell | Radioactivity cpm ± SD |
|---|---|---|
| 1 | 2 | 312 ± 166 |

As will be evident, the $H^3$-thymidine incorporation and hence the DNA synthesis is considerably lower in cell cultures treated with B.B.10 than in cells treated with the control antibodies. The B.B.10 antibody accordingly inhibits the PHA-induced proliferation of activated human T-blasts.

Example 4b

Inhibition of the interleukin-2 induced proliferation of activated T cells with B.B.10 and its Fab fragments The activity of the Fab fragment of B.B.10 was then tested in comparison with the complete B.B.10 molecule with respect to the inhibition of the interleukin-2-induced proliferation of activated T cells as in the foregoing example. The effect of goat antimouse serum (GAM) was also studied. The results are summarized in the following Table 2b. As in the foregoing example, the $H^3$-thymidine incorporation was determined (cpm) at different concentrations of inhibitor (μg/well), with 2 units of interleukin-2 being added to each sample of the medium.

TABLE 2b

| Test substance (in presence of 2 U of IL-2) stimulation | Radioactivity (cpm ± SD) at the stated concentrations | | | |
|---|---|---|---|---|
| | $10^{-3}$ | $10^{-2}$ | $10^{-1}$ | 1 |
| B.B.10 | 6700 | 4700 | 2300 | 1800 |
| Fab | 7000 | 5100 | 3000 | 1400 |
| Fab + 1 μg GAM | 6700 | 5300 | 2700 | 1400 |
| Fab + 1 μg GAM | 7100 | 6700 | 3200 | 1500 |
| GAM 1 μg | 7000 | | | |
| GAM 2 μg | 5700 | | | |

Negative controls: 20.
Positive controls: 6900.

As is evident, the inhibition obtained with the Fab fragment was comparable with B.B.10, meaning that the B.B.10 monoclonal antibody binds monovalently to the interleukin-2 receptor. Its Fab fragment can accordingly also be employed for clinical treatment as its smaller size might ensure better diffusion behavior and possibly even greater effectiveness.

Example 4c

Inhibition of the interleukin-2 induced proliferation of activated T cells with B.B.10 four hours after administration of interleukin-2

$5 \times 10^4$ PHA-activated T cells/well from 3 different donors (donor 1, 2, and 3) were initially incubated for 4 hours at 37° C. in the presence of interleukin-2/well. The amounts of B.B.10 in pg/well are listed in Table 2c. 18 hours later, the $H^3$-thymidine incorporation was determined as in the previous examples (cpm). The results are presented in the following Table 2c.

TABLE 2c

| Concentration IL-2/B.B.10 | Radioactivity (cpm ± SD) | | |
|---|---|---|---|
| | Donor 1 | Donor 2 | Donor 3 |
| Without IL-2 | 667 | 720 | 603 |
| 2 U IL-2 + B.B.10:0 | 8600 | 3300 | 5800 |
| 2 U IL-2 + B.B.10:$10^{-4}$ | 9500 | 3000 | 5200 |
| 2 U IL-2 + B.B.10:$10^{-3}$ | 8200 | 3000 | 5300 |

TABLE 2c-continued

| Concentration IL-2/B.B.10 | Radioactivity (cpm ± SD) | | |
|---|---|---|---|
| | Donor 1 | Donor 2 | Donor 3 |
| 2 U IL-2 + B.B.10:$10^{-2}$ | 3600 | 2000 | 3500 |
| 2 U IL-2 + B.B.10:$10^{-1}$ | 2100 | 1200 | 1600 |
| 2 U IL-2 + B.B.10:1 | 1600 | 960 | 1200 |
| 2 U IL-2 + B.B.10:0 | 11000 | 3600 | 5300 |
| Average 2 U IL-2 + B.B.10:0 | 9800 | 3400 | 5500 |

As is evident, B.B.10 also shows inhibition at low concentrations. This means that B.B.10 inhibits proliferation even after the cells have been activated because interleukin-2 is internalized very rapidly (2 to 3 minutes at 37° C.).

Example 5a

Inhibition of the mixed-lymphocyte reaction $10^5$/ml of peripheral-blood lymphocytes (PBL) were co-cultivated with $10^5$/ml of irradiated (3500 rad) allogenic PBL for 5 days. The control was a syngenic lymphocyte reaction. Appropriate concentrations of monoclonal antibody were added on days 0 and 4. The cultures were labelled with $H^3$-thymidine 18 hours before being harvested. Incorporation into the DNA was measured as in Example 4

The amounts of B.B.10 employed and the associated radioactivity results are presented in Table 3a.

TABLE 3a

| Culture method | MAb B.B.10 μg/well | Radioactivity (cpm ± SD) B.B.10 added on day | |
|---|---|---|---|
| | | 0 | 4 |
| Allogenic culture | 0 | 349 ± 165 | 912 ± 152 |
| Mixed-lymphocyte-culture | 0 | 5544 ± 136 | 5616 ± 146 |
| | $2 \times 10^{-2}$ | 1110 ± 136 | 2296 ± 142 |
| | $2 \times 10^{-1}$ | 619 ± 154 | 1827 ± 139 |
| | 2 | 1054 ± 144 | 1555 ± 145 |

It is evident that the monoclonal antibody B.B.10 effectively inhibits the mixed-lymphocyte response even at low concentrations.

Example 5b

Comparison of the effectiveness of B.B. 10 with that of the known anti-Tac analogues B F2. 33B3.1, Clonab IL-2R, and TB 30 with respect to inhibition of the mixed-lymphocyte The effectiveness of the following monoclonal antibodies on activated T cells was tested on days 0 and 4 as in Example 5a. The control monoclonal antibodies were the Tac analogues B-F2: CRTS, Besancon (France)
33B3.1: Inserm U 110, Marseille (France)
Clonab IL-2R: Biotest AG, Dreieich (Germany), and
TB 30: CLB, Amsterdam (Netherlands).
The results are presented in the following Table 3b.

TABLE 3b

| Antibody | Concentration/well | |
|---|---|---|
| | 0.02 μg | 0.2 μg |
| | Radioactivity (spm ± SD) | |
| | Day 0 | |
| B.B.10 | 1000 | 1100 |
| B-F2 | 1300 | 1100 |
| 33B3.1 | 1800 | 2000 |

TABLE 3b-continued

| | Concentration/well | |
|---|---|---|
| | 0.02 μg | 0.2 μg |
| Antibody | Radioactivity (spm ± SD) | |
| Clonab IL-2R | 1200 | 1500 |
| RB 30 | 1800 | 1800 |
| Negative controls: 398. | Positive controls: 5280 | |
| | Day 4 | |
| B.B.10 | 2300 | 1800 |
| B-F2 | 4600 | 3600 |
| 33B3.1 | 6100 | 4900 |
| Clonab IL-2R | 5400 | 3300 |
| TB 30 | 5700 | 4400 |
| Negative controls: 598. | Positive controls: 6160. | |

These results demonstrate that the known anti-Tac analgues BF-2, 33B3.1, Clonab IL-2R, and TB 30 do not inhibit proliferation at such low doses as does B.B.10 when the monoclonal antibody is added at day 4.

Example 6

Scatchard analysis: determination of the constant affinity

30 μg of purified monoclonal antibody were incubated with Na$^{125}$I (1 m Ci=37 Mbq in 170 μl of PBS. 0.4 mg/ml of chloramine T were added, and the reaction was terminated in 1 minute by adding 10 μl of sodium bisulfite (0.5 μg/μl).

The iodinated monoclonal antibody was chromatographically separated (Sephadex G-25) from free iodine. Its specific radioactivity was 25000 dpm/ng of protein.

$2.5 \times 10^6$ peripheral PHA-activated human T cells were then incubated with various concentrations of $^{125}$I-labelled B.B.10 in 5 ml of RPMI 1640 containing 5% bovine serum albumin.

To prevent unspecific binding, unlabelled B.B.10 monoclonal antibody was added in a 500-fold excess. After 3 hours of incubation at 4° C., the cells were washed 3 times with RPMI 1640 1% bovine serum albumin and the bound radioactivity was measured using an LKB Wallac (1260 Multigamma counter).

The affinity constant was determined from the results

| PHA-activated T-Lymphocytes |
|---|
| Affinity constant, Kd: $1 \times 10^{-9}$ M |

Example 7

Competition of iodated B.B.10 with interleukin-2 on activated T cells

PHA-activated human T cells ($2.5 \times 10^6$) were incubated for 3 hours at 4° C in 1 ml of RPMI 1640 containing 1% bovine serumalbumin and interleukin-2 was added.

The control group consisted of the aforesaid cultures, to which no interleukin-2 was added.

$^{125}$I-labelled B.B.10 was then added. After 1 hour of incubation, the cells were washed and the bound radioactivity measured as in Example 6.

The results are summarized in Table 4.

TABLE 4

| $^{125}$I-labelled B.B.10 μg/ml | B.B.10 μg/ml | Human IL-2 U/ml | Radioactivity cpm ± SD |
|---|---|---|---|
| 0.25 | 125 | 0 | 2395 ± 61 |
| 0.25 | 0 | 0 | 30540 ± 3002 |
| 0.25 | 0 | 500 | 28906 ± 3452 |
| 0.25 | 0 | 2500 | 23976 ± 165 |
| 0.25 | 0 | 5000 | 18477 ± 384 |
| 0.25 | 0 | 10000 | 13047 ± 316 |

It is evident that very high levels of interleukin-2 are necessary to displace the monoclonal antibody (decreasing radioactivity), confirming the high specificity of B.B.10 with respect to the interleukin-2 receptor.

INITIAL CLINICAL TRIALS OF THE MONOCLONAL ANTIBODY B.B.10

Treatment of graft-versus-host disease (GvH) and transplant rejection (HvG) are the major problems of histocompatible and histo-incompatible bone-marrow transplantation.

More recent methods of preventing graft-versus-host disease with polyclonal animal derived antilymphocyte sera, by depleting the donor T cells from the marrow or by chemotherapy, or with anti-T monoclonal antibodies have led in many cases to severe side effects and to rejection of the transplant.

Monoclonal antibodies can be employed to affect the immune response against the transplant in vivo. The use of the monoclonal antibody B.B.10 to treat graft-versus-host disease and transplant-rejection reactions turned out to be surprisingly appropriate and efficient.

The use of this monoclonal antibody renders possible a decrease or completely eliminatition of an ancillary treatment of bone marrow transplantation patients to repress the cellular immune response with other immunosuppressives such as antilymphocyte sera, cyclosporin A or with chemical compounds such as corticosteroids, azathioprine, and methotrexate, which often leads to serious side effects such as higher risk to infections.

In conjunction with the following clinical-emergency indications, 0.1 to 20 mg and preferably 2.5 to 5 mg per day of the monoclonal antibody B.B.10 were administered to the patients within 30 minutes in the form of an intravenous infusion. The dose was selected to attain a plasma level of 0.5 to 5 μg/ml.

The treatment was continued for 3 to 30 days and preferably for 7 to 10 days until the interleukin-2-dependent symptoms subsided. Treatment beyond that point surprisingly turned out to be unnecessary.

EXAMPLE 8

The amounts of the monoclonal antibody B.B.10 (diluted in human albumin) listed in Table 5 were administered at the times cited in the table to a group of 4 patients 4, 11, 23, and 40 years old, 3 of them with graft-versus-host disease.

Patient 1, 11 years old, had a IIIrd-degree graft-versus-host disease accompanied by gastrointestinal dysfunction prior to the treatment. Patients 2 and 3 were suffering a IInd-degree graft-versus-host disease. Patient 4, into whom histoincompatible bone marrow was transplanted and who could not be treated with cyclosporin A due to kidney dysfunctions, was treated prophylactically with the monoclonal antibody B.B.10 immediately after the transplantation.

Table 5 indicates the amounts of B.B.10 administered and the length of the treatment.

TABLE 5

|     | Patient 1 | | Patient 2 | | Patient 3 | | Patient 4 | |
| --- | --- | --- | --- | --- | --- | --- | --- | --- |
| Day | Daily dose MAb mg | Plasma level μg/ml | Daily dose MAb mg | Plasma level μg/ml | Daily dose MAb mg | Plasma level μg/ml | Daily dose MAb mg | Plasma level μg/ml |
| 0 | 7.5 | 0 | 5 | 0 | 5 | 0 | 5 | 0 |
| 1 | 7.5 | 2.9 | 5 | 1.2 | 5 | 0.03 | 5 | 0.07 |
| 2 | 7.5 | 4.7 | 5 | 1.4 | 5 | 0.1 | 5 | 0.14 |
| 3 | 7.5 | 6 | 5 | 2 | 5 | 0.24 | 5 | 0.6 |
| 4 | 7.5 | 7.6 | 5 | 2.2 | 5 | 0.25 | 5 | 0.5 |
| 5 | 7.5 | 8.1 | 5 | 2.3 | 5 | 0.48 | 5 | 0.75 |
| 6 | 7.5 | 8.9 | 5 | 2.9 | 5 | 0.55 | 5 | 1 |
| 7 | 7.5 | 10 | 5 | 3.1 | 5 | 0.96 | 5 | 0.9 |
| 8 |  | 3 | 5 | 3.4 | 5 | 1 | 5 | 1.2 |
| 9 |  | 2.5 | 5 | 4.1 | 5 | 1.05 | 5 | 1.9 |
| 10 |  | 1 |  | n.d. |  | 1.1 | 5 | 2.2 |
| 11 |  | 0 |  | 3.6 |  | 0.5 |  |  |
| 12 |  | 0 |  | 3.1 |  | 0.15 |  |  |
| 13 |  | 0 |  | 1.3 |  | 0 |  |  |
| 14 |  | 0 |  | 0.6 |  | 0 |  |  |
| 15 | 5 | 0 |  | 0.1 |  |  |  |  |
| 16 |  | 1.5 |  |  |  |  |  |  |
| 17 | 5 | 0 |  |  |  |  |  |  |
| 18 |  | n.d. |  |  |  |  |  |  |
| 19 | 5 | 0 |  |  |  |  |  |  |
| 20 |  | 0.15 |  |  |  |  |  |  |
| 21 | 5 | 0 |  |  |  |  |  |  |
| 22 |  | 0.3 |  |  |  |  |  |  |
| 23 | 5 | 0 |  |  |  |  |  |  |
| 24 |  | 0.3 |  |  |  |  |  |  |

(n.d. = not determined)

RESULTS

Surprisingly, the acute symptoms of graft-versus-host disease in Patients 1 through 3 subsided during the first 3 days after the beginning of the monoclonal-antibody treatment. Patient 1 exhibited no further symptoms within 24 days. It became possible to stop treatment of Patient 2 and 3 in 9 days after onset of therapy with complete success. Patient 4, who was treated prophylactically, developed no symptoms of transplant rejection once the treatment had been stopped (day 10).

Although it was not expected, none of the patients showed any prejudicial side effects in correlation to the treatment.

Example 9

A group of 3 patients (5 through 7), 5, 7, and 12 years of age were treated with the monoclonal antibody B.B.10 subsequent to bone-marrow transplantation to control rejection of the transplant.

A histocompatible bone-marrow transplantation was carried out on 2 of these patients and a haploid bone-marrow transplantation on the third one. Due to their age, the dosage of the monoclonal antibody B.B.10 was only 2.5 mg per day.

Table 6 indicates the doses and duration of treatment.

TABLE 6

|     | Patient 5 | | Patient 6 | | Patient 7 | |
| --- | --- | --- | --- | --- | --- | --- |
| Day | Daily dose MAb mg | Plasma level μg/ml | Daily dose MAb mg | Plasma level μg/ml | Daily dose MAb mg | Plasma level μg/ml |
| 0 | 2.5 | 0 | 2.5 | 0 | 2.5 | 0 |
| 1 | 2.5 | 1.7 | 2.5 | 1 | 2.5 | 1.2 |
| 2 | 2.5 | 1.9 | 2.5 | 1.4 | 2.5 | 1.8 |
| 3 | 2.5 | 2.7 | 2.5 | 1.9 | 2.5 | 2.7 |
| 4 | 2.5 | 2.5 | 2.5 | 3.6 | 2.5 | 4.1 |

TABLE 6-continued

|     | Patient 5 | | Patient 6 | | Patient 7 | |
| --- | --- | --- | --- | --- | --- | --- |
| Day | Daily dose MAb mg | Plasma level μg/ml | Daily dose MAb mg | Plasma level μg/ml | Daily dose MAb mg | Plasma level μg/ml |
| 5 | 2.5 | 4.5 | 2.5 | 2.3 | 2.5 | n.d. |
| 6 |  | n.d. | 2.5 | 3.8 | 2.5 | n.d. |
| 7 | 2.5 | 1.5 | 2.5 | n.d. | 2.5 | 3 |
| 8 |  | 0.9 | 2.5 | 4.4 |  | 1.3 |
| 9 | 2.5 | 1.1 |  | 3.9 |  | 2 |
| 10 |  | 1.6 |  | 3.7 |  |  |
| 11 |  | 0.7 |  | 2.6 |  |  |
| 12 |  |  | 0.9 |  |  |  |

(n.d. = not determined)

Results

The rejection reaction was rapidly suppressed in Patient 5, who had received the haploid bone-marrow transplant, and the transplant was accepted.

Patient 6 exhibited no rejection reaction. The transplant was tolerated by the immune system.

In Patient 7, who had received an autologous transplant, no take of the transplant was observed.

The results of the first clinical applications in emergency cases and the data in respect to the affinity and biological activity of the monoclonal antibody B.B.10 indicate that this monoclonal antibody in accordance with the invention can be effectively employed both as a prophylactic agent against and as a therapeutic agent to avoid transplant rejection, graft-versus-host disease, and/or host-versus-graft disease and is definitely superior to all other previously known methods of therapy.

In contrast to previously described treatments with other monoclonal antibodies, no side effects could be observed. This monoclonal antibody can be employed in concentrations lower than the amounts previously employed (cf. J. P. Soulillou, The Lancet 13 [June 13, 1987], 1339). The therapeutic index is accordingly correspondingly higher. Due to its limitation to emergency indications, it has so far not been possible to determine the substance's clinical efficiency, but the effective dose may be even lower than so far observed.

Since the patients were treated with less mouse protein, the probability of antibodies formation to the interleukin-2 receptor antibody B.B.10 is considerably lower and cannot affect the clinical efficiency of this substance.

Concomitant treatment with other drugs associated with severe side effects turns out to be unnecessary.

Example 10

The effectiveness of the monoclonal antibody B.B.10 was also tested in 26 patient suffering from an acute graft-versus-host disease of a high IInd-degree subsequent to bone-marrow transplantation and refractory to treatment with corticoids. 5 mg of B.B.10 per day were administered to each patient for 10 days. No side effects were observed during the treatment.

The results of this study are summarized as follows.

Positive response 18 out of 26 (69.2%), 12 of them with graft-versus-host disease of the IInd-degree and 6 with graft-versus-host disease of the IIIrd-degree.

Partial response 5 out of 26 (19.2%), 1 of them with graft-versus-host disease of the IInd-degree, 2 with graft-versus-host disease of the IIIrd-degree, and 2 with graft-versus-host disease of the IVth-degree.

No response 3 out of 26 (11.5%), 2 of them with graft-versus-host disease of the IIIrd-degree and 1 with graft-versus-host disease of the IVth-degree.

It was observed that the period between the appearance of the graft-versus-host disease and the onset of treatment is extremely important for clinical efficiency. For positive reactions this period averaged 13.7 days, while it averaged 70 days in the event of negative response.

The attached FIGS. 1 through 4 illustrates the level of B.B.10 serum level of 4 patients as a function of the duration of treatment. As is evident, the B.B.10 level remains constant (B.B.10 circulation) over the total time in contrast to other monoclonal antibodies in clinical use.

The specification and examples are illustrative but not limitative to the present invention and other embodiments within the spirit and scope of the invention will suggest themselves to those skilled in the art.

What is claimed is:

1. The hybridoma cell line B.B.10 having CNCM Deposit Number I-752, which produces a monoclonal murine IgG antibody which binds to the 55 kDa subunit of the human interleukin-2 receptor and inhibits or displaces the binding of human interleukin-2 to its receptor, and which blocks an already ongoing allogenic reaction.

2. A hybridoma cell line isolated from that of claim 1, which produces monoclonal antibodies of the major classes $IgG_{2a}$, $IgG_{2b}$ $IgG_3$ or IgM which bind to the 55 kDa subunit of the human interleukin-2 receptor and inhibits or displaces the binding of human interleukin-2 to its receptor, and which blocks an already ongoing allogenic reaction.

3. A monoclonal antibody of class $IgG_1$, obtained from the cell line of claim 1 and characterized by specific immunological binding to human cells which express the interleukin-2 receptor.

4. Chimeras of monoclonal antibodies according to claim 3, having a human constant region and a murine variable region.

5. Chimeras of monoclonal antibodies according to claim 4, having murine hypervariable regions.

* * * * *